United States Patent
Matson (10) Patent No.: US 7,291,122 B2
(45) Date of Patent: *Nov. 6, 2007

(54) HEMOFILTRATION METHODS FOR TREATMENT OF DISEASES IN A MAMMAL

(75) Inventor: James R. Matson, Dallas, TX (US)

(73) Assignee: Immunocept, L.L.C., Dallas, TX (US)

( * ) Notice: Subject to any disclaimer, the term of this patent is extended or adjusted under 35 U.S.C. 154(b) by 129 days.

This patent is subject to a terminal disclaimer.

(21) Appl. No.: 10/843,933

(22) Filed: May 12, 2004

(65) Prior Publication Data

US 2005/0029193 A1 Feb. 10, 2005

Related U.S. Application Data

(63) Continuation-in-part of application No. 09/815,675, filed on Mar. 23, 2001, now Pat. No. 6,736,972.

(60) Provisional application No. 60/191,788, filed on Mar. 24, 2000.

(51) Int. Cl.
*A61M 1/34* (2006.01)
*B01D 61/00* (2006.01)
*B01D 61/14* (2006.01)

(52) U.S. Cl. .................. 604/6.09; 210/650; 210/651; 210/660; 604/4.01; 604/5.01; 604/5.04; 604/6.11

(58) Field of Classification Search ............ 210/195.1, 210/195.2, 252, 258, 294, 295, 416.1, 428, 210/433.1, 434, 645, 650, 651, 660, 661, 210/663, 669; 422/44, 261; 435/2, 85.2, 435/219, 226; 514/1, 2, 12, 21; 530/380, 530/381, 382, 383, 384; 604/4.01, 5.01, 604/5.04, 6.09, 6.11

See application file for complete search history.

(56) References Cited

U.S. PATENT DOCUMENTS 2,682,268 A 6/1954 Ryan et al. ................. 604/262

(Continued)

FOREIGN PATENT DOCUMENTS

EP 0 098 392 A2 6/1983

(Continued)

OTHER PUBLICATIONS

Seiichi Mochizuki et al.'s "Extran transport through asymmetric ultrafilitration membranes: Comparison with hydrodynamic models". Jouranl of Membrane Science, 68 (1992) pp. 21-41, 1992.

(Continued)

*Primary Examiner*—John Kim
(74) *Attorney, Agent, or Firm*—Baker Botts L.L.P.

(57) ABSTRACT

A hemofiltration system and method to treat an Inflammatory Mediator Related Disease in a mammal, including chronic and acute diseases, include a hemofilter and an adsorptive device. The hemofilter removes ultrafiltrate from a blood stream extracted from the mammal to create a filtered blood stream and an ultrafiltrate stream. The adsorptive device may include one or more adsorbent materials and may be used to adsorb inflammatory mediators from the ultrafiltrate stream received from the hemofilter to create a post adsorption ultrafiltrate stream. The post adsorption ultrafiltrate stream may be selectively combined with the filtered blood stream and together with the filtered blood stream may be returned to the mammal.

21 Claims, 6 Drawing Sheets

U.S. PATENT DOCUMENTS

| | | | | |
|---|---|---|---|---|
| 4,000,072 A | 12/1976 | Sato et al. | ............... | 210/315 |
| 4,172,071 A | 10/1979 | De Maeyer et al. | ........ | 260/112 |
| 4,180,460 A | 12/1979 | Calari | ................. | 210/182 |
| 4,248,736 A | 2/1981 | Fuchigami et al. | ......... | 252/428 |
| 4,313,831 A | 2/1982 | Lehmann et al. | ............ | 210/341 |
| 4,355,906 A | 10/1982 | Ono | ............................ | 366/274 |
| 4,362,155 A | 12/1982 | Skurkovich | ................ | 128/214 |
| 4,402,940 A | 9/1983 | Nose et al. | .................. | 424/101 |
| 4,581,141 A | 4/1986 | Ash | ............................ | 210/502 |
| 4,596,779 A | 6/1986 | Ono | ............................ | 435/286 |
| 4,614,513 A | 9/1986 | Bensinger | ...................... | 604/6 |
| 4,618,343 A | 10/1986 | Polaschegg | .................. | 604/29 |
| 4,708,799 A | 11/1987 | Gerlach et al. | ........ | 210/500.23 |
| 4,781,068 A | 11/1988 | Pradelli | .................... | 73/861.38 |
| 4,784,974 A | 11/1988 | Butt | ......................... | 210/321.8 |
| 4,844,810 A | 7/1989 | Richalley et al. | ........... | 210/646 |
| 4,863,609 A | 9/1989 | Schnabel et al. | ............ | 210/641 |
| 4,872,983 A | 10/1989 | Dimantoglou et al. | ...... | 210/500 |
| 4,874,522 A | 10/1989 | Okamoto et al. | ........... | 210/645 |
| 4,897,189 A | 1/1990 | Greenwood et al. | ......... | 210/195 |
| 4,900,720 A | 2/1990 | Kotitschke | .................... | 514/21 |
| 4,968,432 A | 11/1990 | Antwiler | ...................... | 210/677 |
| 5,044,901 A | 9/1991 | Fumero et al. | ............. | 417/474 |
| 5,211,850 A | 5/1993 | Shettigar et al. | ............ | 210/645 |
| 5,286,449 A | 2/1994 | Kuroda et al. | ................. | 422/48 |
| 5,450,516 A | 9/1995 | Pasquali et al. | ............. | 385/115 |
| 5,523,096 A | 6/1996 | Okarma et al. | .............. | 424/489 |
| 5,536,412 A | 7/1996 | Ash | ............................ | 210/645 |
| 5,571,418 A | 11/1996 | Lee et al. | .................... | 210/651 |
| 5,578,223 A | 11/1996 | Bene et al. | .................... | 210/85 |
| 5,661,124 A | 8/1997 | Hoffman et al. | ................ | 514/6 |
| 5,683,584 A | 11/1997 | Wenthold et al. | ........... | 210/500 |
| 5,744,042 A | 4/1998 | Stange et al. | ............... | 210/645 |
| 5,762,798 A | 6/1998 | Wenthold et al. | ........... | 210/500 |
| 5,808,181 A | 9/1998 | Wamsiedler et al. | ........... | 73/38 |
| 5,846,419 A | 12/1998 | Nederlof | ................... | 210/323.1 |
| 5,851,394 A | 12/1998 | Shibata et al. | .............. | 210/500 |
| 5,855,782 A | 1/1999 | Falkenhagen et al. | ... | 210/323.1 |
| 5,858,238 A | 1/1999 | McRea et al. | .............. | 210/645 |
| 5,905,141 A | 5/1999 | Rausch et al. | .............. | 530/385 |
| 5,919,369 A | 7/1999 | Ash | ............................ | 210/645 |
| 5,919,444 A | 7/1999 | Norman, Jr. | ................ | 424/85.2 |
| 5,931,802 A | 8/1999 | Yoshida et al. | ................. | 604/4 |
| 5,944,684 A | 8/1999 | Roberts et al. | ................. | 604/5 |
| 5,945,337 A | 8/1999 | Brown | ........................ | 435/389 |
| 5,986,062 A | 11/1999 | Ohmura et al. | ............. | 530/363 |
| 6,008,199 A | 12/1999 | Grinnell et al. | ............... | 514/21 |
| 6,022,477 A | 2/2000 | Luo et al. | ................... | 210/645 |
| 6,039,946 A | 3/2000 | Strahilevitz | .............. | 424/140.1 |
| 6,042,784 A | 3/2000 | Wamsiedler et al. | ........... | 422/44 |
| 6,156,734 A | 12/2000 | Grinnell et al. | ............... | 514/21 |
| 6,191,114 B1* | 2/2001 | Vallespi et al. | ............... | 514/13 |
| 6,193,681 B1 | 2/2001 | Davidner et al. | .......... | 604/6.08 |
| 6,280,632 B1 | 8/2001 | Polaschegg | ................. | 210/739 |
| 6,287,516 B1 | 9/2001 | Matson et al. | ................ | 422/44 |
| 6,497,675 B1 | 12/2002 | Davankov | ................... | 604/6.09 |
| 6,595,943 B1 | 7/2003 | Burbank | ................... | 604/5.01 |
| 6,667,299 B1 | 12/2003 | Ahlem et al. | ................ | 514/178 |
| 6,730,266 B2* | 5/2004 | Matson et al. | ................. | 422/44 |
| 6,736,972 B1 | 5/2004 | Matson | ....................... | 210/650 |
| 6,905,688 B2 | 6/2005 | Rosen et al. | ............. | 424/192.1 |
| 2004/0199099 A1* | 10/2004 | Matson et al. | ............. | 604/6.09 |
| 2004/0228829 A1 | 11/2004 | Roberts et al. | ............. | 424/78.1 |
| 2006/0129082 A1 | 6/2006 | Rozga | ........................ | 604/6.04 |

FOREIGN PATENT DOCUMENTS

| | | |
|---|---|---|
| EP | 0 787 500 A1 | 8/1997 |
| GB | 2124511 A | 2/1984 |
| WO | 95/04559 | 2/1995 |

OTHER PUBLICATIONS

International Search Report PCT/US02/23603 5 pages, mailed Apr. 15, 2003.

International Search Report PCT/US03/07784 6 pages, mailed Jul. 17, 2003.

Konstantin et al. "Artificial Liver" from Artificial Organs vol. 16 Issue pp. 235-242 Blackwell Publications Inc. Boston MA 1992 International Society for Artificial Organs, 1992.

"Hemodiafiltration in Two Chambers Without Replacement Fluid: A Clinical Study" by C. Sanz-Moreno and J. Botella, Artificial Organs vol. 19 No. 5 1995.

International Search Report for PCT/US/99/15426.

Bende et al., "Elimination of endotoxin from the blood by extracorporeal activated charcoal hemoperfusion in experimental canine enotoxin shock". Circ Shock, vol. 19(2), pp. 239-244, 1986.

Nagaki et al., "Removal of endotoxin and cytokines by absorbents and the effect of plasma protein binding". Int Journal of Artificial Organs, vol. 14(1), pp. 43-50, Jan. 1991.

Nagaki et al., "In vitro plasma perfusion through adsorbents and plasma ultrafiltration to remove endotoxin and cytokines". Circ Shock, vol. 38(3), pp. 182-188, Nov. 1992.

Huges et al., "Use of sorbent columns and haemofiltration in fulminant hepatic failure". Blood Purif. vol. 11(3), pp. 163-169, 1993.

Nagaki et al., "Clearance and tissue distribution of staphylococcal enterotoxin A in the rat and potential use of adsorbents for removal from plasma", Journal of Med. Microbiology, vol. 38(5), pp. 354-359, May 1993.

Tetta et al., "Continuous plasma filtration coupled with sorbents". Kidney Int. Suppl., vol. 53, pp. S186-S189, May 1998.

Pusey et al., "Experimental models of plasma perfusion". Journal of Clin. Apheresis, vol. 6(2), pp. 99-102, 1991.

Geiger et al., "Biochemical assessment and clinical evaluation of bilirubin adsorbent column (BR-350) in critically ill patients with intractable jaundice". Int. Journal of Artificial Organs, vol. 15(1), pp. 35-39, Jan. 1992.

Tetta et al., "Removal of cytokines and activated complement components in an experimental model of continuous plasma filtration coupled with sorbent adsorption". Nephrol Dial. Transplant, vol. 13(6), pp. 1458-1464, Jun. 1998.

Rinaldo Bellomo et al., Nomenclature for Continuous Renal Replacement Therapy Atlas of Hemofiltration, p. 11-14.

"A Dangerous Error in the Dilution of 25 Percent Albumin", The New England Journal of Medicine, vol. 338:1226-1227, No. 17, http://content.nejrn.org/cgi/content/extract/338/17/1226, 2 pgs.

ZLB Behring, Albumin (Human) USP, 25%, Albuminar -25, RX Only, 7 pgs.

* cited by examiner

HEMOFILTRATION METHODS FOR TREATMENT OF DISEASES IN A MAMMAL

RELATED APPLICATION

This application is a Continuation-In-Part of U.S. patent application Ser. No. 09/815,675 filed Mar. 23, 2001 entitled "Method and System for Providing Therapeutic Agents with Hemofiltration for Reducing Inflammatory Mediator Related Diseases", now U.S. Pat. No. 6,736,972 which claims priority from Provisional Patent Application Ser. No. 60/191,788 filed Mar. 24, 2000.

This application is related to application Ser. No. 09/858,210 filed May 15, 2001, entitled Method and System for Colloid Exchange Therapy filed by David Radunsky et al., now U.S. Pat. No. 6,787,040; and application Ser. No. 09/912,904 filed Jul. 25, 2001, entitled Hemofiltration Systems, Methods and Devices Used to Treat Inflammatory Mediator Related Disease filed by James R. Matson et al., now U.S. Pat. No. 6,730,266.

TECHNICAL FIELD

The present invention relates generally to systems, methods and devices using hemofiltration for treatment of both chronic and acute Inflammatory Mediator Related Diseases. More specifically, the present invention relates to use of hemofiltration techniques, including adsorptive devices and therapeutic agents to treat such diseases.

BACKGROUND

Inflammatory Mediator Related Diseases often result from excessive activation of the inflammatory response. The inflammatory response consists of the interaction of various cell systems (e.g., monocyte/macrophage, neutrophil, and lymphocytes) and various humoral systems (e.g., cytokines, coagulation, complement, and kallikrein/kinin). Each component of each system may function as an effector (e.g., killing pathogens, destroying tissue, etc.), a signal (e.g., most cytokines), or both. Humoral elements of the inflammatory response are known collectively as inflammatory mediators. Inflammatory mediators include various cytokines (e.g., tumor necrosis factor ("TNF"); the interleukins; interferon, etc.), various prostaglandins (e.g., PG $I_2$, $E_2$, Leukotrienes), various clotting factors (e.g., platelet activating factor ("PAF")), various peptidases, reactive oxygen metabolites, and various poorly understood peptides which cause organ dysfunction (e.g., myocardial depressant factor ("MDF")). These compounds interact as a network with the characteristics of network preservation and self-amplification. Some of these compounds, such as MDF and peptidases, are directly injurious to tissue; other compounds, such as cytokines, coordinate destructive inflammation.

The systemic inflammatory response with its network of systems (e.g., monocytes/macrophages, complement, antibody production, coagulation, kallikrein, neutrophil activation, etc.) is initiated and regulated through the cytokine system and other inflammatory mediators. (Cytokines are generally thought of as a subgroup of inflammatory mediators.) The cytokine system consists of more than 200 known molecules each of which activates or suppresses one or more components of the immune system or one or more other cytokines in the network. The cytokine network is the dominant control system of the immune response. The primary sources of cytokines are monocytes/macrophages, endothelial cells, and similar cells.

Key characteristics of the cytokine system are as follows: (i) cytokines are chemical signals coordinating immune system and associated systemic activities; (ii) commonly, two or more cytokines will trigger the same action providing a "fail safe" response to a wide variety of different stimuli (the systemic inflammatory response is critical to the individual's survival; these redundant control signals assure a systemic response which does not falter); (iii) cytokine and inflammatory mediator concentrations (usually measured in blood) therefore increase in order to stimulate, control, and maintain the inflammatory response proportionally to the severity of the injury or infection; and (iv) as severity of injury or infection increases, the cytodestructive activity of the system increases. Therefore, high concentrations of cytokines and inflammatory mediators measured in the patient's blood, that are sustained over time correlate with the patient's risk of death.

The general strategy of most treatments is to identify what is conceived to be a key or pivotal single cytokine or inflammatory mediator. This single target cytokine or inflammatory mediator is then inactivated in an attempt to abate the inflammatory response. The most widely applied technologies used to inactivate cytokines or inflammatory mediators is binding with monoclonal antibodies or specific antagonists. Monoclonal antibodies and specific antagonists are used because they effectively bind the target cytokines or inflammatory mediators, or their receptors, usually in an "all or none" blockade.

This strategy is problematic for two reasons. First, the cytokine system is essential to mobilize the inflammatory response, and through it, the host immune response. If the cytokine system were blocked, death would ensue from unhealed injury or infection. Second, the cytokine and inflammatory mediator signals which make up the control network of the immune response consist of many redundant control loops to assure the "fail safe" initiation and continuation of this critical response. Such a redundant, self-amplifying system is generally not effectively controlled by blocking one point, such as one cytokine or inflammatory mediator.

Patients with life threatening illness are cared for in hospitals in the intensive care unit. These patients may be seriously injured from automobile accidents, etc., have had major surgery, have suffered a heart attack, or may be under treatment for serious infection, cancer, or other major disease. While medical care for these primary conditions is sophisticated and usually effective, a significant number of patients in the ICU will not die of their primary disease. Rather, a significant number of patients in the ICU die from a secondary complication known commonly as sepsis or septic shock. Medically, sepsis and septic shock and their effects are sometimes referred to as Systemic Inflammatory Response Syndrome, Multiple Organ System Dysfunction Syndrome, Multiple Organ System Failure, and Compensatory Anti-inflammatory Response Syndrome.

In short, medical illness, trauma, complication of surgery, and any human disease state, if sufficiently injurious to the patient, may elicit Systemic Inflammatory Response Syndrome/Multiple Organ System Dysfunction Syndrome/Multiple Organ System Failure or Compensatory Anti-inflammatory Response Syndrome. The systemic inflammatory response within certain physiologic limits is beneficial. As part of the immune system, the systemic inflammatory response promotes the removal of dead tissue, healing of injured tissue, detection and destruction of cancerous cells as they form, and mobilization of host defenses to resist or to combat infection.

When stimulated by injury or infection, the systemic inflammatory response may cause symptoms which include fever, increased heart rate, and increased respiratory rate. This symptomatic response constitutes Systemic Inflammatory Response Syndrome. If the stimulus to the systemic inflammatory response is very potent, such as massive tissue injury or major microbial infection, then the inflammatory response is can be excessive. This excessive response can cause injury or destruction to vital organ tissue and may result in vital organ dysfunction, which may be manifested in many ways, including a drop in blood pressure, deterioration in lung function, reduced kidney function, and other vital organ malfunction. This condition is known as Multiple Organ System Dysfunction Syndrome. With very severe or life threatening injury or infection, the inflammatory response is extreme and can cause extensive tissue damage with vital organ damage and failure. These patients will usually die promptly without the use of ventilators to maintain lung ventilation, drugs to maintain blood pressure and strengthen the heart, and, in certain circumstances, artificial support for the liver, kidneys, coagulation, brain and other vital systems. This condition is known as Multiple Organ System Failure. These support measures partially compensate for damaged and failed organs, they do not cure the injury or infection or control the extreme inflammatory response which causes vital organ failures.

In recent years, it is increasingly recognized that Systemic Inflammatory Response Syndrome/Multiple Organ System Dysfunction Syndrome/Multiple Organ System Failure/ Compensatory Anti-inflammatory Response Syndrome exists in phases. In particular, an early pro-inflammatory phase, which is recognized as Systemic Inflammatory Response Syndrome, usually occurs within hours or a very few days of significant injury or infection; Compensatory Anti-inflammatory Response Syndrome occurs later. Systemic Inflammatory Response Syndrome and Compensatory Anti-inflammatory Response Syndrome may also appear in repeating and alternate cycles, or concurrently.

As noted previously, the pro-inflammatory response is critical to host recovery and survival (by healing injury and eliminating infection), but when extreme this response causes vital organ dysfunction or failure. In biology, it is common for one response to be counter balanced by another response; these compensatory responses or systems allow restoration of balance and return the organism (e.g., the patient) to homeostasis. Compensatory Anti-inflammatory Response Syndrome is associated with the abatement of the excesses inflammatory mediators characteristic of Systemic Inflammatory Response Syndrome, however Compensatory Anti-inflammatory Response Syndrome itself is often extreme and results in immune suppression. Systemic Inflammatory Response Syndrome and Compensatory Anti-inflammatory Response Syndrome are each associated with respective characteristic inflammatory mediators. The immune suppression of Compensatory Anti-inflammatory Response Syndrome is very commonly associated with secondary infection. This secondary infection then elicits another Systemic Inflammatory Response Syndrome, often worse and more destructive than the first. In patients, it is commonly this second episode of Systemic Inflammatory Response Syndrome which is lethal.

Both Systemic Inflammatory Response Syndrome and Compensatory Anti-inflammatory Response Syndrome are mediated by excesses of either pro-inflammatory and anti-inflammatory mediators, respectively. Hemofiltration may be as beneficial to Compensatory Anti-inflammatory Response Syndrome as to Systemic Inflammatory Response Syndrome. However, in Systemic Inflammatory Response Syndrome the improvement may be affirmatively observed by improvement in pulmonary and cardio-circulatory function and survival, whilst in Compensatory Anti-inflammatory Response Syndrome it may be observed negatively, by non-occurrence of secondary infection and secondary Systemic Inflammatory Response Syndrome. Both Systemic Inflammatory Response Syndrome and Compensatory Anti-inflammatory Response Syndrome may be monitored in a limited way, by monitoring their respective inflammatory mediators in blood, lung fluid or other body fluid. Systemic Inflammatory Response Syndrome and Compensatory Anti-inflammatory response Syndrome may occur concurrently as a mixed or an overlapping disorder.

In the United States of America each year, Systemic Inflammatory Response Syndrome/Multiple Organ System Dysfunction Syndrome/Multiple Organ System Failure afflicts approximately 700,000 patients and results in about 200,000 deaths. Overall, depending on the number of organ systems failing, the mortality rate of Multiple Organ System Failure ranges generally from 40 to 100%. For instance, if three or more vital organs fail, death results in about 90% of cases. Systemic Inflammatory Response Syndrome/Multiple Organ System Dysfunction Syndrome/Multiple Organ System Failure and Compensatory Anti-inflammatory Response Syndrome are the most common cause of death in intensive care units and are the thirteenth most common cause of death in the United States of America. Systemic Inflammatory Response Syndrome/Multiple Organ System Dysfunction Syndrome/Multiple Organ System Failure and Compensatory Anti-inflammatory Response Syndrome costs about $15 billion yearly for supportive care. In addition, the incidence of Systemic Inflammatory Response Syndrome/Multiple Organ System Dysfunction Syndrome/Multiple Organ System Failure and Compensatory Anti-inflammatory Response Syndrome are on the rise; reported cases increased about 139% between 1979 and 1987. This increase is due to an aging population, increased utilization of invasive medical procedures, immuno-suppressive therapies (e.g. cancer chemotherapy) and transplantation procedures.

Inflammatory Mediator Related Diseases include both acute problems, as well as chronic problems.

Chronic inflammatory diseases of the joints and skin such as lupus, fibromyalgia, pemphigoid and rheumatoid arthritis and other rheumatoid conditions generally result from chromic inflammation. These diseases may therefore benefit from ultrafiltration to remove their inflammatory mediators. Removal of redundant mediators may be particularly helpful.

Chronic degenerative disease of the nervous system may be mediated by abnormal levels of serum and cerebrospinal fluid antibodies. For example, abnormal levels of antibodies have been detected in multifocal motor neuropathy and chronic inflammatory demyelinating polyneuropathy. The immune response has also been implicated in multiple sclerosis, Guillain-Barre syndrome, systemic lupus erythematosis, and cryobulinemic vasculitis. Patients with chronic degenerative diseases of the nervous system may, therefore, benefit from ultrafiltration of the blood to lower antibody levels, control inflammation or lower levels of other abnormal proteins or substances correlated with a particular degenerative neuromuscular disease.

Existing techniques of hemofiltration have been developed as a technique to control overhydration and acute renal failure in unstable ICU patients. Existing hemofiltration techniques may use a hemofilter of various designs and materials. For example, the material may consist of a cellulose derivative or synthetic membrane (e.g., polysulfone, polyamide, etc.) fabricated as either a parallel plate or hollow fiber filtering surface. Because the blood path to, through, and from the membrane is low resistance, the patient's own blood pressure drives blood through the filter circuit. In these hemofiltration applications, the hemofilter is part of a blood circuit. In passive flow hemofiltration, arterial blood flows through a large bore cannula, into plastic tubing leading to the filter; blood returns from the filter through plastic tubing to a vein. This is known as arteriovenous hemofiltration. Alternatively a blood pump is used, so that blood is pumped from either an artery or a vein to the filter and returned to a vein. This is known as pumped arteriovenous hemofiltration or pumped venovenous hemofiltration. Ultrafiltrate collects in the filter jacket and is drained through the ultrafiltrate line and discarded. Ultrafiltrate flow rates are usually 250 ml–2000 ml/hour. In order to prevent lethal volume depletion, a physiologic and isotonic replacement fluid is infused into the patient concurrently with hemofiltration at a flow rate equal to or less than the ultrafiltrate flow rate. The balance of replacement fluid and ultrafiltrate is determined by the fluid status of the patient.

Treatment of certain diseases by filtration of blood is well established medical practice. Dialysis, using dialysis filters, which remove molecules with molecular weights up to 5,000 to 10,000 Dalton, is used to treat chronic and some acute renal failure. Conventional hemofiltration, discussed below, is used to treat acute renal failure, and in some cases, chronic renal failure. Plasmapheresis, using plasma filters or centrifuge techniques which remove molecules with molecular weights of 1,000,000 to 5,000,000 Dalton or more, is used to treat diseases associated with high molecular weight pathologic immunoglobulins or immune complexes, (e.g., multiple myeloma, lupus vasculitis, etc.).

During filtration of protein-containing solutions, colloids or suspensions, or blood, the accumulation of protein as a gel or polarization layer occurs on the membrane surface. This gel layer typically reduces effective pore size, reducing the filterable molecular weights by roughly 10–40%. Therefore, pore sizes selected are somewhat larger than needed, anticipating a reduction in effective size. Thus, present membranes allow filtration and removal of excess water, electrolytes, small molecules and nitrogenous waste while avoiding loss of albumin or larger proteins. These membranes are well-suited to their accepted uses, that is, treatment of overhydration and acute renal failure in unstable ICU patients.

Observations in ICU patients indicate that hemofiltration, in addition to controlling overhydration and acute renal failure, is associated with improvements in lung function and cardiovascular function. None of these improvements has been associated with shortened course of ventilator therapy, shortened ICU stay, or improved survival. The usual amount of ultrafiltrate taken in the treatment of overhydration and acute renal failure is 250 to 2000 ml/hour, 24 hours a day. A few published observations have suggested that higher amounts of ultrafiltrate brought about greater improvements in pulmonary and cardiovascular status; these have resulted in the development of a technique known as high volume hemofiltration. In high volume hemofiltration, from 2 to 9 liters/hour of ultrafiltrate are taken for periods of from 4 to 24 hours or more.

There is however great hesitance to use high volume hemofiltration for the following reasons: (i) the high volumes (currently 24–144 liters/day) of ultrafiltrate require equally high volumes of sterile, pharmaceutical grade replacement fluid; at these high volumes, errors in measuring ultrafiltrate coming out and replacement fluid flowing into the patient could cause injurious or lethal fluid overload or volume depletion; (ii) the high volume of ultrafiltrate removed could filter out of the blood desirable compounds from the patient resulting in dangerous deficiencies; (iii) large volumes of warm (body temperature) ultrafiltrate flowing out of the patient, and large volumes of cool (room temperature) replacement fluid flowing into the patient can cause thermal stress or hypothermia; and (iv) high volumes of replacement fluid add considerable expense to the therapy.

High volume hemofiltration, as currently practiced, uses conventional hemofilters with pore sizes which provide a molecular weight cut off of 30,000 Daltons and occasionally of 50,000 Daltons. The device and process described in U.S. Pat. No. 5,571,418 generally contemplates the use of large pore hemofiltration membranes with pore sizes to provide molecular weight exclusion limits of 100,000 to 150,000 Daltons. With these higher molecular weight cutoffs, these membranes are designed to remove a wider range of different inflammatory mediators; these large pore membranes should remove excess amounts of all known inflammatory mediators. These large pore hemofiltration membranes have been demonstrated in animal studies to be superior to conventional hemofilter membranes in improving survival time in a swine model of lethal *Staphylococcus aureus* infection (Lee, PA et al. *Critical Care Medicine* April 1998). However, it may be anticipated that in high volume hemofiltration, the large pore membranes may also remove more desirable compounds thus increasing the risk of the negative side effects of high volume hemofiltration.

Other techniques used in the past to treat inflammatory diseases include hemodialysis and plasmapheresis. Hemodialysis is well suited to fluid and small solute (less the 10,000 Daltons) removal. However hemodialysis membranes remove very few inflammatory mediators (only those smaller than 5000 to 10,000 Daltons) and so have been ineffective in improving patient condition in Systemic Inflammatory Response Syndrome/Multiple Organ Dysfunction Syndrome/Multiple Organ System Failure. In the unstable ICU patient, hemodialysis commonly results in rapid deterioration of cardiovascular function and pulmonary function requiring premature termination of the dialysis procedure. Hemodialysis has also been associated with increasing the occurrence of chronic renal failure in survivors of Systemic Inflammatory Response Syndrome/Multiple Organ Dysfunction Syndrome/Multiple Organ System Failure. Hemofiltration was specifically developed to avoid these complications of hemodialysis and has been very successful in doing so.

Plasmapheresis can be done with both membrane based and centrifugation based techniques. Plasmapheresis separates plasma and all that plasma contains from blood, leaving only formed elements. The removed plasma is usually replaced by either albumin solution or fresh frozen plasma. The removed plasma would contain all inflammatory mediators. However all desirable substances, many adapted to the patient's current condition, are also removed, often with injurious or lethal effects.

Consequently, the additional methods for treatment of Inflammatory Mediator Related Diseases are needed. Furthermore, while high volume hemofiltration holds some promises, it is unworkable in its present form and is overly dangerous.

SUMMARY

In accordance with teachings of the present invention a method and system for treating Inflammatory Mediator Related Diseases in mammals using a hemofilter is disclosed.

In selected embodiments, the invention may relate to the treatment of acute or chronic problems. It may also include use of a therapeutic agent in connection with the hemofilter. An adsorptive device may also be included. Embodiments of the present invention may be particularly beneficial when used in large pore hemofiltration systems.

According to one aspect of the present invention, a hemofiltration system for treating Inflammatory Mediator Related Diseases is disclosed. The system includes a hemofilter to receive blood and remove inflammatory mediators from the blood. The system may further include at least one therapeutic agent used in association with the hemofilter to reduce adverse inflammatory mediator effects.

In a particularized form the system may further include a 100 to 150 kiloDalton hemofilter.

In a further particularized form the system may include an adsorptive device associated with the hemofilter.

In another particularized form, the system may include a biological agent to reduce adverse inflammatory mediator effects, or reduce other adverse effects.

In a further particularized form, the system may include a pharmaceutical agent to reduce adverse inflammatory mediator effects.

According to another aspect of the present invention, a method for treating inflammatory mediator related diseases is disclosed. The method includes receiving blood from a mammal and filtering the blood using a hemofilter wherein the hemofilter removes inflammatory mediators from the blood. The method may further include providing at least one therapeutic agent wherein the therapeutic agent reduces adverse inflammatory mediator effects.

In a particularized form, the therapeutic agent may include a biological agent.

In another particularized form, the therapeutic agent may include a pharmaceutical agent.

In a further particularized form, the hemofilter may be configured as a 100 to 150 kiloDalton hemofilter.

In another particularized form, an adsorptive device associated with the hemofilter may be provided.

According to another aspect of the present invention, a system and method are provided for hemofiltration of blood from mammals having a chronic inflammatory disease, such as chronic inflammatory skin and joint disease and chronic neuromuscular disease, especially those with debilitating diseases refractory to existing medical therapies.

Specific embodiments of the present invention include a hemofilter, blood and ultrafiltrate lines, and an adsorptive device having one or more chambers containing adsorbent material of one or more types. The hemofilter receives a stream of blood removed from the mammal and removes ultrafiltrate from the stream of blood and thereby creates a stream of filtered blood, which is eventually returned to the mammal, and a stream of ultrafiltrate. The ultrafiltrate typically includes plasma water, electrolytes, peptides and small proteins. The blood peptides and proteins removed from the blood by the hemofilter and found in the ultrafiltrate have a molecular size smaller than the pore size of the hemofilter. Most inflammatory mediators are included in this group. The ultrafiltrate is then provided to the adsorptive device.

The hemofilter may be made of a biocompatible material. In particular, the hemofilter may include a membrane and a jacket. In specific embodiments, the membrane and jacket may include biocompatible materials.

The adsorptive device may incorporate an encasement jacket along with one or more chambers containing adsorbent material of one or more types. The adsorptive device may receive the stream of ultrafiltrate and selectively or nonselectively remove inflammatory mediators that cause Inflammatory Mediator Related Diseases from the ultrafiltrate to create a stream of post adsorption ultrafiltrate.

The adsorptive device may be designed to be placed in the line transferring ultrafiltrate removed by the hemofilter to adsorb inflammatory mediators from the ultrafiltrate, producing post adsorption ultrafiltrate. The stream of post adsorption ultrafiltrate may eventually be combined or reinfused, in whole or in part, with the stream of filtered blood and returned to the mammal. The above systems and methods may be used with acute or chronic diseases, as appropriate.

One technical advantage of some embodiments of the present invention includes providing rapid stabilization of septic shock to increase survival rate of a mammal.

Another technical advantage of some embodiments of the present invention includes abating excessive and destructive inflammatory activity which characterizes septic shock or other Inflammatory Mediator Related Diseases.

The immune system has many redundant cytokine and inflammatory mediator control loops; several of these loops must be down-regulated to achieve systemwide disease control and to see improvement in the symptoms of various diseases including chronic skin, joint and neuromuscular disease. Various embodiments of the present invention address this task.

A further technical advantage of specific embodiments includes increasing the effectiveness of therapeutic agents as adjunctive therapy to hemofiltration.

Certain embodiments of the invention allow the safe use of two-stage high volume hemofiltration, which may result in improved mammal survival. These embodiments may avoid or minimize dangerous fluid balance errors inherent to conventional high volume hemofiltration, avoid or minimize the risk of depletion of desirable humoral compounds, avoid or minimize thermal stress and hypothermia, and avoid or minimize the cost of excessive amounts of replacement fluid.

Moreover, the use of an adsorptive device including adsorbent material(s) in selected embodiments provides additional advantages. First, with respect to the risk of high fluid flux in high volume hemofiltration, the adsorbent device adsorbs inflammatory mediators from the ultrafiltrate, thus removing them from the ultrafiltrate; the post adsorption ultrafiltrate may then be reinfused, in whole or in part, back into the mammal. Because post adsorption ultrafiltrate may be returned to the mammal, in whole or in part, the amount of replacement fluid needed to preserve fluid balance in the mammal may be sharply reduced (to the amount of ultrafiltrate discarded), or eliminated entirely. The volumes of ultrafiltrate discarded and replacement fluid infused may be limited to those indicated by the mammal's state of edema (over hydration) and/or needs to accommodate medicinal or nutrient solutions; typically 2 to 6 liters per day. These lower volumes of fluid flux (about 2 to 6 liters per day) may be safely managed by existing pump technology; pumping errors with these small volumes are well tolerated.

Second, with respect to the risk of depletion of desirable compounds in high volume hemofiltration, because all or most of the ultrafiltrate may be returned to the mammal (as post adsorption ultrafiltrate), and because adsorbent material may be selected with as narrow a range of adsorbed substances as possible and focused on inflammatory mediators, the loss of desirable substances may be minimized.

Third, with respect to the risk of hypothermia in high volume hemofiltration, because warm (body temperature) ultrafiltrate may be returned to the mammal, the amount of cool (room temperature) replacement fluid needed may be sharply reduced. This may control or eliminate the heat loss which would otherwise occur with discard of ultrafiltrate and also control or eliminate the cooling which would occur by the infusion of cool replacement fluid. In this way, the stress of hypothermia may be controlled or eliminated. Fourth, with respect to the expense, the cost of replacement fluid varies widely depending on markets, contract arrangements and other considerations. However, $2 to $10 per liter are typical costs. Thus, high volume hemofiltration could create an incremental cost of from $96 to $1,500 per day. By reinfusion of post adsorption ultrafiltrate following adsorption of inflammatory mediators, and thereby reducing the need for all or most replacement fluid, this incremental cost may be reduced or eliminated.

In summary, high volume hemofiltration is a technique that may significantly improve symptoms and survival in chronic disease, however, high volume hemofiltration creates new and substantial risks and expenses. Various embodiment of the present invention may eliminate or sharply reduce some or all of these risks and expenses, and make high volume hemofiltration, as well as low volume hemofiltration much safer and more cost effective in mammals suffering from Inflammatory Mediator Related Diseases.

Other advantages of the invention described herein are explained in greater detail below.

BRIEF DESCRIPTION OF THE DRAWINGS

A more complete understanding of specific embodiments of the present invention and advantages thereof may be acquired by referring to the following description taken in conjunction with the accompanying drawings, in which like reference numbers indicate like features, and wherein.

DETAILED DESCRIPTION

As a point of reference, the following terms and definitions are provided. Although definitions are provided herein, one skilled in the art may understand the various terms, based on further information provided herein or background knowledge, to encompass subject matter beyond that set forth in these definitions.

The term "hemofiltration" refers to a process of filtering blood by a membrane with separation of all formed elements, all proteins larger than effective pore size of the membrane, and retained plasma water and solute from ultrafiltrate. Blood components not part of the ultrafiltrate are normally returned to the mammal.

The term "ultrafiltrate" refers to the filtered plasma water, solute, molecules and other materials, including target peptides and proteins containing inflammatory mediators and smaller than effective pore size of the membrane in a hemofilter.

The term "Systemic Inflammatory Response Syndrome" refers to the excessive and dysfunctional elaboration of inflammatory mediators in a mammal, which results in an excessive and injurious inflammatory response.

The term "Multiple Organ Dysfunction Syndrome" refers to Systemic Inflammatory Response Syndrome causing injury or destruction to vital organ tissue and resulting in vital organ dysfunction, which may be manifested in many ways, including a drop in blood pressure, deterioration in lung function, reduced kidney function, and other vital organ malfunction.

The term "Multiple Organ System Failure" refers to the clinical syndrome of vital organ dysfunction or failure due to tissue injury resulting from Systemic Inflammatory Response Syndrome. Its mortality rate is approximately 40–100%.

The term "Inflammatory Mediator Related Disease" refers to any disease state characterized by injurious or lethal excess production of inflammatory mediators. Diseases commonly included in this category include lupus erythematosis, hemolytic uremic syndrome, bullous pemphigoid, pemphigus vulgaris, sepsis, Systemic Inflammatory Response Syndrome/Multiple Organ Dysfunction Syndrome/Multiple Organ System Failure, Compensatory Anti-inflammatory Response Syndrome, fibromyalgia, rheumatoid conditions, chronic neuromuscular disease such as multiple sclerosis, Guillain-Barre syndrome, cryobulinemic vasculitis, chronic inflammatory demyelinating polyneuropathy, macular degeneration, chronic neuromuscular and multifocal motor neuropathy, and certain coagulation disorders. Various other diseases presently known or discovered in the future may also fall within the category of Inflammatory Mediator Related Diseases.

The term "Compensatory Anti-inflammatory Response Syndrome" refers to the clinical condition which occurs in association with or in response to Systemic Inflammatory Response Syndrome, which is a reduction, compensatory or otherwise, of the immune responsiveness of the host. If the reduced immune responsiveness of Compensatory Anti-inflammatory Response Syndrome is sufficiently severe, then anergy and increased susceptibility to infection may lead to complicating new infections in the host. Compensatory Anti-inflammatory Response Syndrome is associated with circulating anti-inflammatory mediators including interleukins-4, -10, -11, and -13, soluble receptors of TNF, and the like. Concentration of these anti-inflammatory inflammatory mediators in the blood of the host may correlate with the severity of Compensatory Anti-inflammatory Response Syndrome.

The term "inflammatory mediators" refers to a heterogeneous group of chemicals synthesized and released by human tissue. Inflammatory mediators include cytokines, prostaglandins, oxygen metabolites, kinins, complement factors, various clotting factors, various peptidases, various peptides, various proteins, and various toxic peptides. The molecular weight range of known inflammatory mediators is typically between 1,000–500,000 Daltons. Inflammatory mediators may include both pro-inflammatory and anti-inflammatory mediators.

The term "hemofilter" refers to the filter used in hemofiltration. It may be configured in a number of ways, such as a series of parallel plates or as a bundle of hollow fibers. The blood path is typically from a blood inlet port, through the fibers or between the plates, then to a blood outlet port. Filtration of blood occurs at the membrane with ultrafiltrate forming on the side of the membrane opposite the blood. This ultrafiltrate may accumulate inside the body of the filter enclosed by the filter jacket. This jacket typically has an ultrafiltrate drainage port.

The term "large pore hemofiltration" refers to the use of a membrane or other types of filtration media which may remove albumin from a mammal's blood stream. For some applications, a large pore hemofilter may have molecular weight exclusion limits equal to or greater than approximately 69,000 Daltons and may be used to treat Inflammatory Mediator Related Diseases in accordance with teachings of the present invention. For some applications, large pore hemofiltration, performed in accordance with teachings of the present invention, may permit removal of more albumin from a mammal's blood stream than some previous hemofiltration techniques and devices. However, teachings of the present invention may be used to substantially reduce or eliminate negative effects from removing increased amounts of albumin or other desirable compounds from a mammal's blood stream during large pore hemofiltration. In some uses, large pore hemofiltration may treat liver failure using a hemofilter of up to 500–1 million kD.

The term "large pore hemofilter" refers to a hemofilter satisfactory for use in providing large pore hemofiltration in accordance with teachings of the present invention. "High Volume hemofiltration" includes hemofiltration in which from 2 to 9 liters/hour of ultrafiltrate are taken for periods of from 4 to 24 hours or more.

Figure 1A:
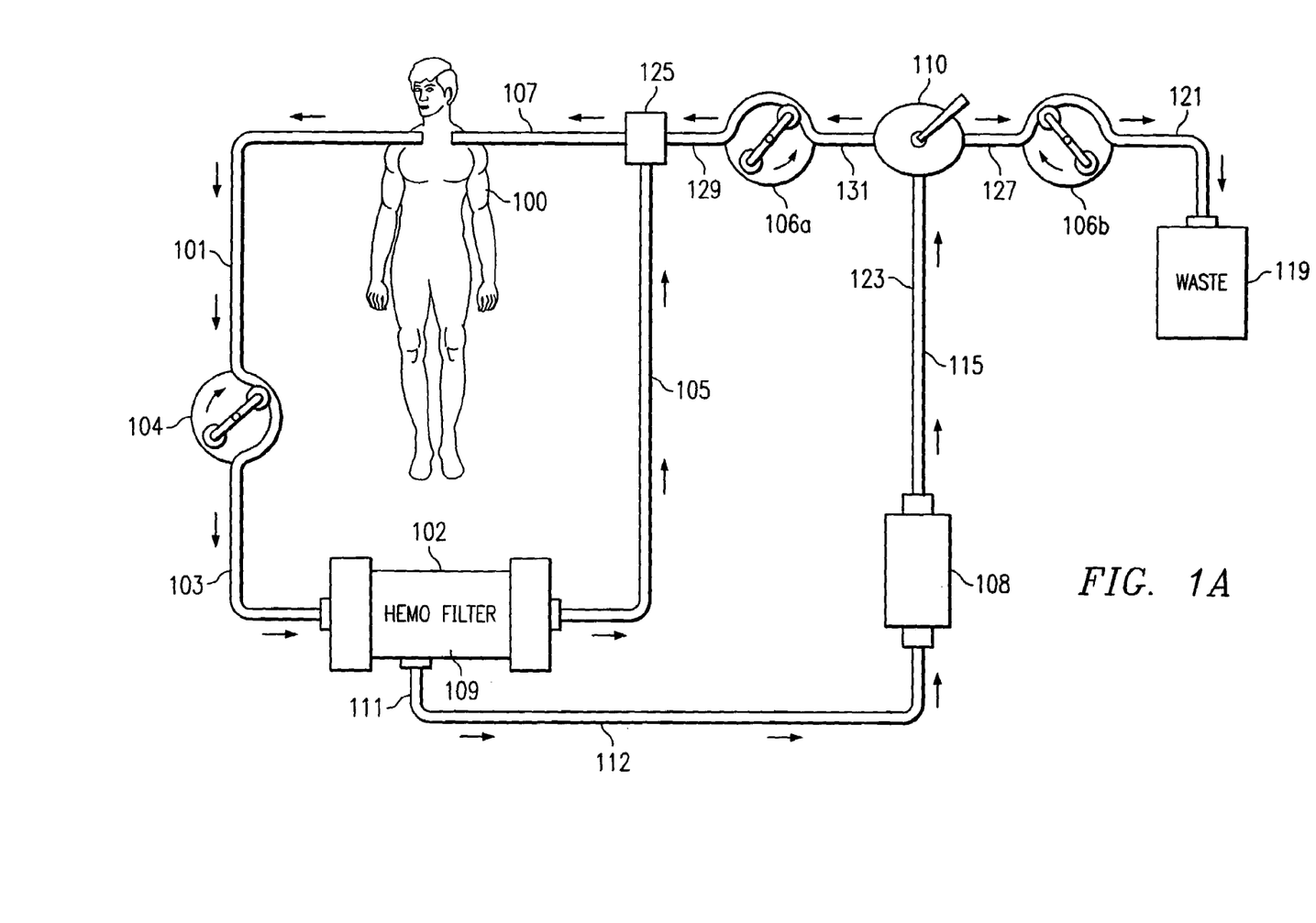
FIG. 1A is a schematic of the physical layout of various components of a specific embodiment, including mammal 100, such as a human, hemofilter 102, blood pump 104, first ultrafiltrate pump 106a and second ultrafiltrate pump 106b, adsorptive device 108 having one or more chambers containing adsorbent material of one or more types, three-way stop cock or first three-way joint 110, second three-way joint 125, and associated tubing.
Figure 1B:
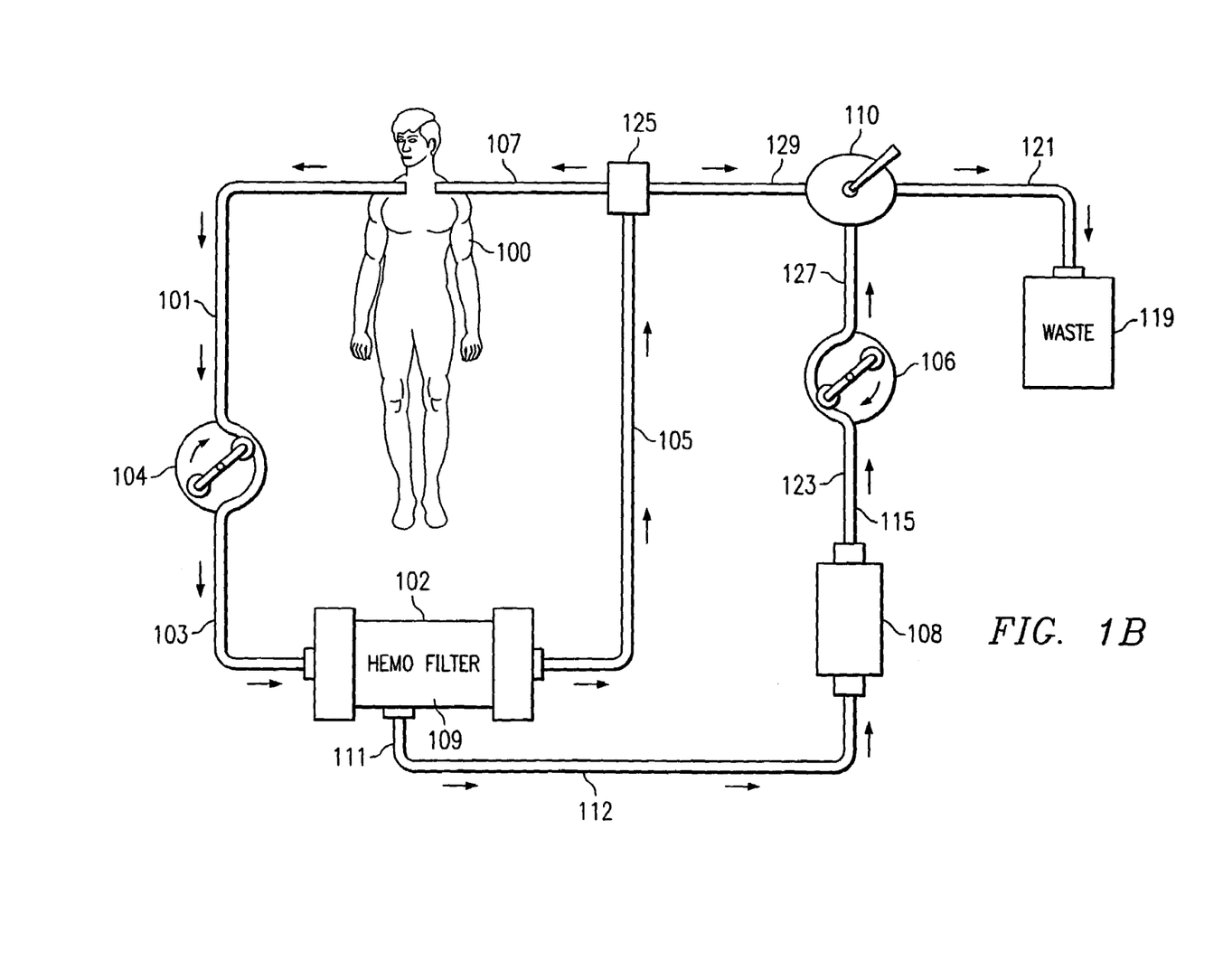
FIG. 1B is a schematic of the physical layout of various components of a specific embodiment, including mammal 100, such as a human, hemofilter 102, blood pump 104, single ultrafiltrate pump 106, adsorptive device 108 having one or more chambers containing adsorbent material of one or more types, three-way stop cock or first three-way joint 110, second three-way joint 125, and associated tubing.
Figure 2:
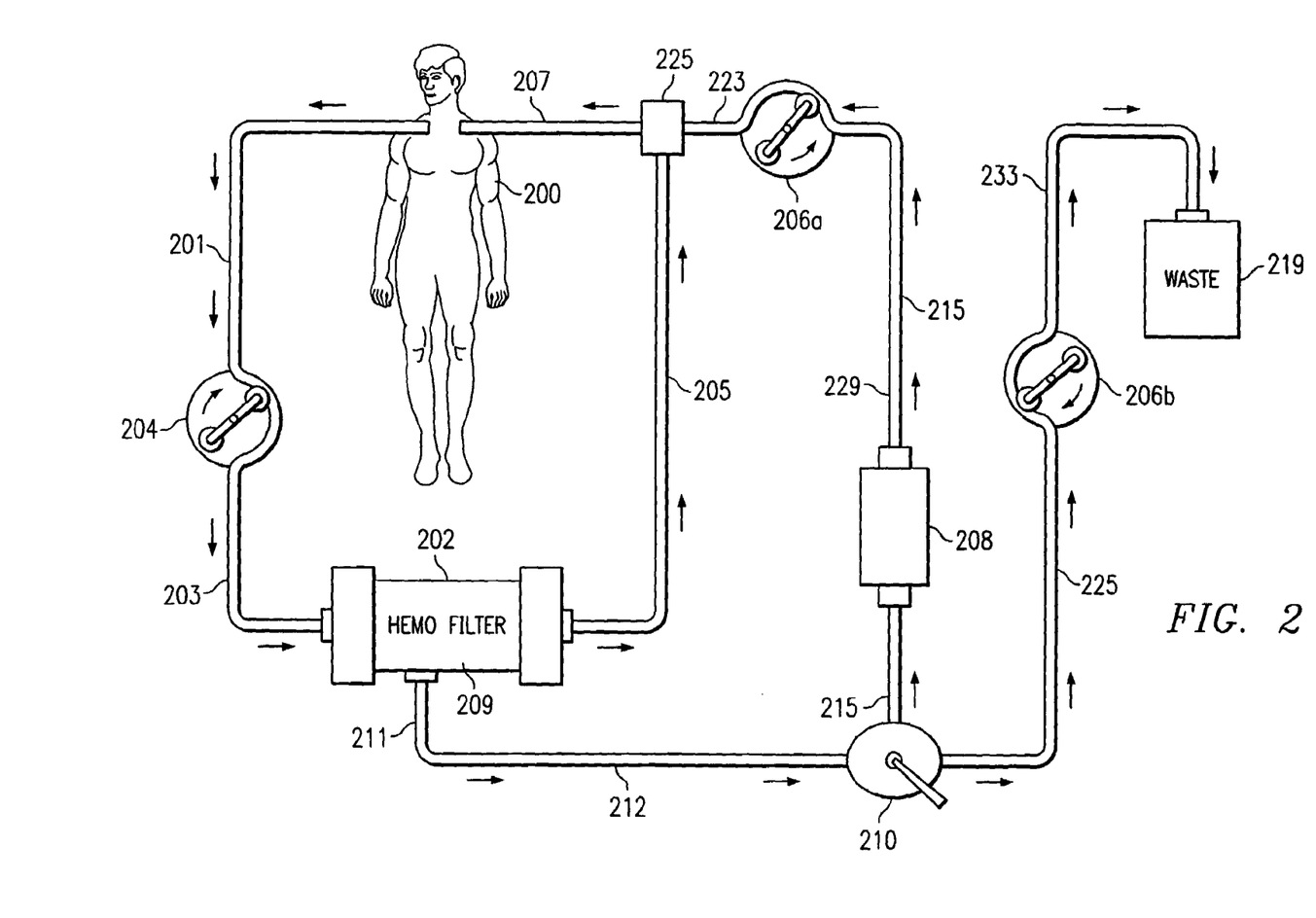
FIG. 2 is a schematic of an alternate physical layout of various components of a specific embodiment, including mammal 200, such as a human, hemofilter 202, blood pump 204, first ultrafiltrate pump 206a and second ultrafiltrate pump 206b, adsorptive device 208 having one or more chambers containing adsorbent material of one or more types, three-way stop cock or first three-way joint 210, second three-way joint 225, and associated tubing.
Figure 3:
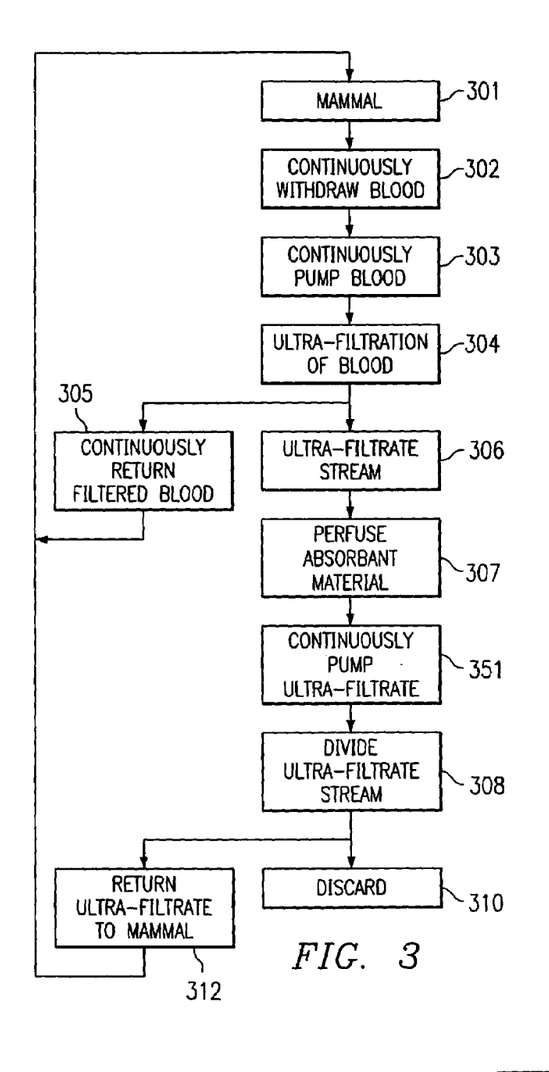
FIG. 3 is a diagram showing the system flow of a specific embodiment shown in FIG. 1A.
Figure 4:
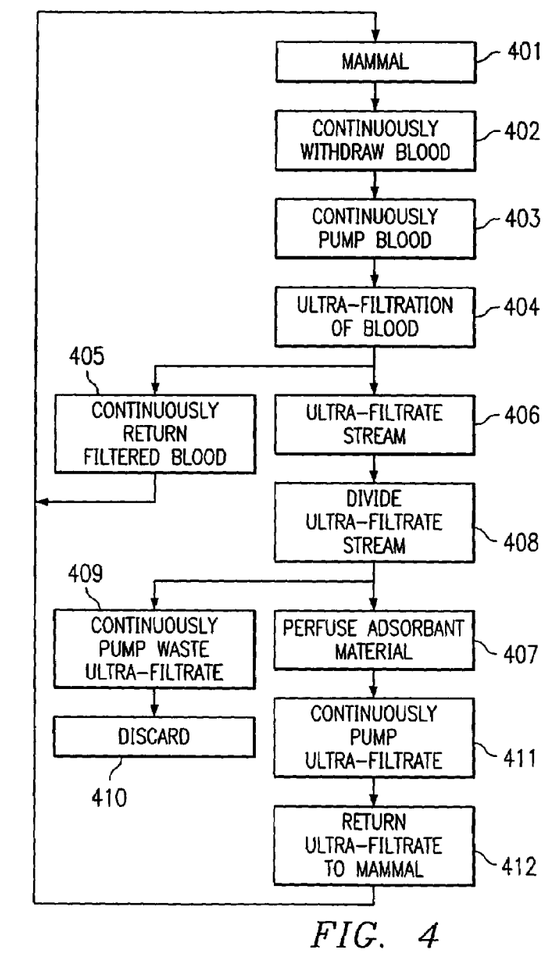
FIG. 4 is a diagram showing the system flow of a specific embodiment shown in FIG. 2.

FIG. 1A is a schematic of the physical layout of various components of a specific embodiment, including mammal 100, such as a human, hemofilter 102, blood pump 104, first ultrafiltrate pump 106a, second ultrafiltrate pump 106b, adsorptive device 108 having one or more chambers containing adsorbent material of one or more types, three-way stop cock or first three-way joint 110, second three-way joint 125, and associated tubing. FIG. 1B is similar to FIG. 1A, except that single ultrafiltrate pump 106 is used in lieu of first ultrafiltrate pump 106a and second ultrafiltrate pump 106b. Both FIGS. 1A and 1B position three-way stop cock or first three-way joint 110 in such a manner that it divides ultrafiltrate stream downstream from adsorptive device 108. FIG. 2 is an alternate schematic of the physical layout of various components of a specific embodiment shown in FIGS. 1A and 1B, except that three-way stop cock or first three-way joint 210 divides the ultrafiltrate stream before adsorptive device 208. FIG. 3 is a diagram showing the system flow of a specific embodiment shown in FIG. 1A. FIG. 4 is a diagram showing the system flow of a specific embodiment shown in FIG. 2.

Steps 301 and 302 (in FIG. 3) and steps 401 and 402 (in FIG. 4) show blood being continuously withdrawn from mammal 100 (in FIGS. 1A and 1B) and mammal 200 (in FIG. 2), such as human and directed to blood pump 104 (in FIGS. 1A and 1B) and blood pump 204 (in FIG. 2), such as a human via first tubing 101 (in FIGS. 1A and 1B) and first tubing 201 (in FIG. 2). Specifically, step 303 (in FIG. 3) and step 403 (in FIG. 4) show the continuous pumping of blood by blood pump 104 into hemofilter 102 via second tubing 103 (in FIGS. 1A and 1B) and by blood pump 204 into hemofilter 202 via second tubing 203 (in FIG. 2). Mammal 100 (in FIGS. 1A and 1B) and mammal 200 (in FIG. 2), such as a human, may have a major blood vessel cannulated allowing for the continuous withdrawal of blood by blood pump 104 (in FIGS. 1A and 1B) and blood pump 204 (in FIG. 2). As shown in steps 304 and 306 (in FIG. 3) and steps 404 and 406 (in FIG. 4), hemofilter 102 ultra-filtrates blood extracted from mammal 100, such as a human (in FIGS. 1A and 1B) and hemofilter 202 ultra-filtrates blood extracted from mammal 200, such as a human (in FIG. 2). And, step 305 (in FIG. 3) and step 405 (in FIG. 4) returns blood filtered by hemofilter 102 to mammal 100 via third tubing 105 and fourth tubing 107 in FIGS. 1A and 1B and by hemofilter 202 to mammal 200 via third tubing 205 and fourth tubing 207 in FIG. 2.

Referring to FIGS. 1A, 1B, and 2, ultrafiltration is a filtration process in which blood cells and blood proteins with a molecular size larger than the pore size of hemofilter membrane 109 (in FIGS. 1A and 1B) and yhemofilter membrane 209 (in FIG. 2) are retained in the blood path. The composition of hemofilter membrane 109 (in FIGS. 1A and 1B) and hemofilter membrane 209 (in FIG. 2) may include biocompatible material, such as polysulfone, polyacrylonitrile, polymethylmethacrylate, polyvinyl-alcohol, polyamide, polycarbonate, cellulose derivatives, etc., but is not limited to these materials. The jacket of the hemofilter may include a biocompatible material, such as polycarbonate, but is not limited to polycarbonate. Hemofilter membrane 109 (in FIGS. 1A and 1B) and hemofilter membrane 209 (in FIG. 2) may be organized as a parallel plate membrane or as a membrane hollow fiber.

Specific embodiments may use a hemofilter incorporating the techniques and materials discussed in U.S. Pat. No. 5,571,418, which is herein incorporated by reference, which discusses the use of large pore hemofiltration membranes for hemofiltration processes. Hemofilter membrane 109 in FIGS. 1A and 1B and hemofilter membrane 209 in FIG. 2 may include large pore hemofiltration membranes, which are may be fabricated from any biocompatible material suitable for the purpose such as polysulfone, polyacrylonitrile, polymethylmethacrylate, polyvinyl-alcohol, polyamide, polycarbonate, cellulose derivatives, etc., but without limitation to these materials.

As shown in step 304 in FIG. 3, hemofilter membrane 109 (in FIGS. 1A and 1B) sieves a fraction of plasma water, electrolytes, blood peptides and proteins with a molecular size smaller than the pore size of the membrane to form ultrafiltrate stream 111 (in FIGS. 1A and 1B), which is directed to adsorptive device 108 (in FIGS. 1A and 1B), which has one or more chambers containing adsorbent material of one or more types, via fifth tubing 112 (in FIGS. 1A and 1B). As shown in step 307 in FIG. 3, adsorptive device 108 is perfused by ultrafiltrate stream 111. Similarly, as shown in step 404 in FIG. 4, hemofilter membrane 209 (in FIG. 2) sieves a fraction of plasma water, electrolytes, blood peptides and proteins with a molecular size smaller than the pore size of the membrane to form ultrafiltrate stream 211 (in FIG. 2), which is directed to adsorptive device 208 (in FIG. 2), which has one or more chambers containing adsorbent material of one or more types, via fifth tubing 212, and sixth tubing 215 (in FIG. 2). As shown in step 407 in FIG. 4, adsorptive device 208 is perfused by ultrafiltrate stream 211.

As shown in steps 308 in FIG. 3, ultrafiltrate stream 115 (in FIGS. 1A and 1B) is divided at three-way stop cock or first three-way joint 110 (in FIGS. 1A and 1B), after adsorptive device 108 in FIGS. 1A and 1B. As shown by step 408 in FIG. 4, ultrafiltrate stream 211 (in FIG. 2) is divided at three-way stop cock or first three-way joint 210 (in FIG. 2), before adsorptive device 208 in FIG. 2.

Specifically, in FIG. 1A, after three-way stop cock or first three-way joint 110 divides post-adsorptive ultrafiltrate stream 115, discard ultrafiltrate stream 127 is directed toward second ultrafiltrate pump 106b and to waste reservoir 119 and return ultrafiltrate stream 131 is directed toward first ultrafiltrate pump 106a and on to mammal 100, such as a human. In FIG. 1B, ultrafiltrate stream 115 is directed toward single ultrafiltrate pump 106 and discard ultrafiltrate stream 121 is directed to waste reservoir 119 and return ultrafiltrate stream 129 is returned to mammal 100, such as a human. In FIG. 2, ultrafiltrate stream 211 is directed toward three-way stop cock 210 and discard ultrafiltrate stream 221 is directed toward second ultrafiltrate pump 206b and then onto waste reservoir 219 and return ultrafiltrate stream 229 is directed toward first ultrafiltrate pump 206a and eventually returned to mammal 200, such as human.

Figure 5A:
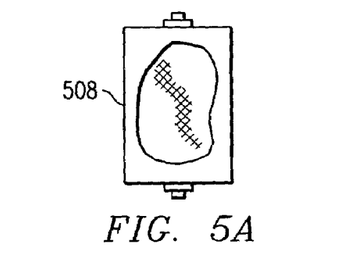
FIGS. 5A, 5B, and 5C are diagrams showing alternate specific embodiments of adsorbent device 108 (in FIGS. 1A and 1B) and adsorptive device 208 (in FIG. 2)
Figure 5B:
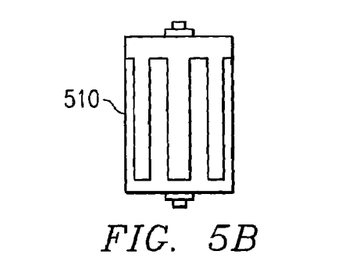
Figure 5C:
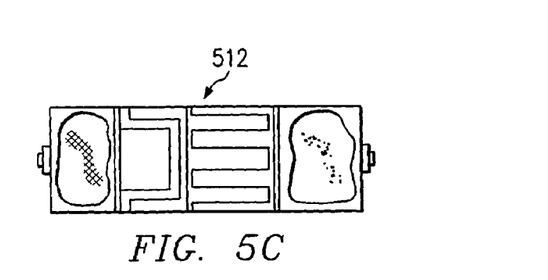

Adsorptive device 108 (in FIGS. 1A and 1B) and adsorptive device 208 (in FIG. 2) have one or more chambers containing adsorbent material(s). The adsorbent material(s) may be fixed or contained within the respective adsorbent device. Typically none will pass into the ultrafiltrate stream or return to mammal 100 (in FIGS. 1A and 1B) and mammal 200 (in FIG. 2), such as a human. The adsorbent materials used in specific embodiments may be coated or uncoated. The nature of the adsorbent materials used in specific embodiments is such that solutes to be adsorbed may be bound to the adsorbent materials. As shown in FIG. 5A, 5B, and 5C, adsorbent material is presented to ultrafiltrate flows by structures such as rods or plates, or through structures such as beads or porous matrix of any configuration effective in presentation of adsorptive material(s) to ultrafiltrate stream, or through one or more chambers containing immobilized particulate, beaded or fragmented adsorbent material. Adsorbent materials may include, but are not limited to: silica, activated charcoal, nonionic or uncharged resins or polymers, ionic or charged resins or polymers, immobilized polymyxin B, anion exchange resin or polymer, cation exchange resin or polymer, neutral exchange resin or polymer, immobilized monoclonal antibodies, immobilized inflammatory mediators receptors, immobilized specific antagonists, cellulose and its derivatives, synthetic materials, polysulfone, polyacrylonitrile, polymethylmethacrylate, polyvinyl-alcohol, polyamide, polycarbonate, polystyrene-derivative fibers, Xigris® and the like or any combination thereof.

The selection of adsorbent materials may depend on the inflammatory mediators to be removed. Specific embodiments may use polymyxin to remove endotoxin, anti-TNF antibody to remove TNF, or polyacrylonitrile to remove interleukin 1-beta and TNF, among other adsorbents. Adsorbents may be both specific and nonspecific. Adsorbents may also be used in various combinations as the mammal's condition and stage of disease warrant.

FIGS. 5A, 5B, and 5C are diagrams showing selected embodiments of adsorptive device 108 (in FIGS. 1A and 1B) and adsorptive device 208 (in FIG. 2), both of which have one or more chambers containing adsorbent material of one or more types. Adsorbent materials vary widely in their adsorptive capacity as well as types and conditions of substances adsorbed. Inflammatory mediators are of many different chemical types (e.g. peptides, lipids) and each inflammatory mediator's charge and plasma binding (e.g., specific or nonspecific circulating soluble receptors) may vary and affect characteristics of how they may be adsorbed during the course of any Inflammatory Mediator Related Disease. For this reason, various adsorbent materials may be used in a single adsorptive device in order to provide the range of chemical binding characteristics and capacity needed for removal of many inflammatory mediators from the ultrafiltrate.

Adsorbent materials may be of different chemical and physical types. Particulate adsorbent materials (e.g. charcoal; beads of polysulfone, polyacrylonitrile, polymethylmethacrylate, polyvinyl-alcohol, polyamide, polycarbonate, cellulose derivatives, and similar materials; liposomes, etc.) may be coated or uncoated, but are usually encased in a porous flexible mesh sac or rigid porous containment jacket which allows free access of perfusing fluid (e.g. ultrafiltrate) but contains the particles and prevents them from being carried back to the mammal in the ultrafiltrate stream.

Some adsorbents (e.g. silica gel) lend themselves to being cast or otherwise fabricated in various rigid or semirigid configurations (e.g. rods, plates etc.), which allow for effective and convenient presentation of ultrafiltrate containing inflammatory mediators to the adsorbent material.

Other adsorbents (e.g. monoclonal antibodies, inflammatory mediators receptors, specific antagonists, polymyxin B) may best be affixed to a supporting matrix of biocompatible material (e.g. polycarbonate and the like) for presentation of adsorbent material to the ultrafiltrate stream containing inflammatory mediators. The matrix of biocompatible material may be configured to allow effective and convenient presentation of ultrafiltrate containing inflammatory mediators to the affixed adsorbent material.

Depending on physical and chemical compatibilities of the adsorbent materials, and the requirements of adequate ultrafiltrate flow, adsorbent device 108 (in FIGS. 1A and 1B) and adsorbent device 208 (in FIG. 2) may be configured as one chamber containing one or more adsorbent materials, as shown in adsorptive device 508 in FIG. 5A and adsorptive device 510 in FIG. 5B, or separated into multiple chambers each containing one or more adsorbent materials, as shown in adsorptive device 512 in FIG. 5C. Adsorbent devices 508 (in FIG. 5A), 510 (in FIG. 5B), and 512 (in FIG. 5C) have an inlet port to which the ultrafiltrate tubing which carries the ultrafiltrate from hemofilter 108 (in FIGS. 1A and 1B) and hemofilter 208 (in FIG. 2) may be attached to provide ultrafiltrate flow to adsorbent devices 508, 510, or 512. Ultrafiltrate flow through adsorbent device 508 (in FIG. 5A), 510 (in FIG. 5B), and 512 (in FIG. 5C), perfuses the adsorbent materials allowing for adsorption of inflammatory mediators, and flows out of the adsorbent device through an outlet port.

Referring to FIG. 5C, where a multiple chamber configuration is used for adsorptive device 512, the chambers may be separated by a screen or other porous barrier which retains the adsorbent materials or combinations of adsorbent materials in their separate compartments and allows free flow of ultrafiltrate through adsorptive device 512. An alternative embodiment utilizes separate, exchangeable modules each containing an adsorbent material or adsorbent materials. A module or a combination of modules may be inserted into the adsorbent device to provide for the adsorption of different types of inflammatory mediators as the condition of the mammal may require. Although not shown, adsorbent device 108 (in FIGS. 1A and 1B) and adsorptive device 208 (in FIG. 2) may be incorporated into or combine with hemofilter 102 (in FIGS. 1A and 1B) and hemofilter 202 (in FIG. 2), respectively. In this embodiment ultrafiltrate formed at the hemofilter membrane passes into the hemofilter jacket, the hemofilter jacket incorporates the adsorptive materials in one or more chambers and ultrafiltrate flows through the adsorbent materials. Ultrafiltrate transfers from the combined hemofilter/adsorbent device through an outlet port to post adsorbent ultrafiltrate tubing.

The amount of blood continuously pumped may be operator determined and may depend on the condition of mammal 100 (in FIGS. 1A and 1B) and mammal 200 (in FIG. 2), such as a human, and the needs of effective hemofiltration. The amount of blood continuously removed may be determined on a case by case basis. The flow rate, the amount of blood removed and the duration of the hemofiltration therapy may be determined by the weight, the age and the nature and severity of the illness in the mammal. Typically, blood flow rates may range from 100 to 200 ml/minute. The rate of ultrafiltration may depend on the nature and severity of illness and may be indexed to body weight, total body water and/or clinical indices of disease management (e.g., pulmonary function, cardiovascular status, etc.). Typically, total ultrafiltrate flow rate is 1 to 9 liters/hour of which from 0 to 2 liters/hour may be discarded. The discard rate may be determined by the fluid balance requirements of the mammal. The amount of ultrafiltrate discarded may be determined by the operator as the operator judges the needs of mammal 100 and mammal 200, such as a human, for fluid removal. All ultrafiltrate not discarded may returned to mammal 100 (in FIGS. 1A and 1B) and mammal 200 (in FIG. 2), such as a human.

With respect to the tubing used in specific embodiments, the blood pump tubing, ultrafiltrate tubing, etc., may be made of a biocompatible material, such as polyvinylchloride, but is not limited to this material. The tubing may be flexible and have outside or inside diameters complementary to the appropriate hemofilter connections, adsorptive device connections, joints, stop cocks, or pump heads.

Specifically, with respect to the tubing in FIG. 1A, first tubing 101 transfers blood from mammal 100, such as a human to blood pump 104; second tubing 103 transfers blood from blood pump 104 to hemofilter 102; third tubing 105 transfers the filtered blood filtered by hemofilter 102 to second three-way joint 125; fourth tubing 107 transfers the filtered blood along with the post adsorption ultrafiltrate to mammal 100, such as a human; fifth tubing 112 transfers the ultrafiltrate to adsorptive device 108; sixth tubing 123 transfers the post adsorption ultrafiltrate to three-way stop cock or second three-way joint 110; seventh tubing 131 transfers post adsorption ultrafiltrate to first ultrafiltrate pump 106a; eighth tubing 129 transfers post adsorption ultrafiltrate from first ultrafiltrate pump 106a to second three-way joint 125 joining fourth tubing 107 which transfers filtered blood along with the post adsorption ultrafiltrate to the mammal; ninth tubing 127 transfers post adsorption ultrafiltrate to second ultrafiltrate pump 106b; and tenth tubing 121 transfers post adsorption ultrafiltrate from second ultra filtrate pump 106b to waste reservoir 119. First ultrafiltrate pump 106a and associated tubing implement steps 311 and 312 in FIG. 3; second ultrafiltrate pump 106b, waste reservoir 119, and associated tubing implement steps 309 and 310 in FIG. 3.

With respect to the tubing in FIG. 1B, first tubing 101 transfers blood from mammal 100, such as a human, to blood pump 104; second tubing 103 transfers blood from blood pump 104 to hemofilter 102; third tubing 105 transfers the filtered blood filtered by hemofilter 102 to second three-way joint 125; fourth tubing 107 transfers the filtered blood along with the post adsorption ultrafiltrate to mammal 100, such as a human; fifth tubing 112 transfers the ultrafiltrate to adsorptive device 108; sixth tubing 123 transfers the post adsorption ultrafiltrate or ultrafiltrate stream 115 to single ultrafiltrate pump 106; seventh tubing 127 transfers post adsorption ultrafiltrate from ultrafiltrate pump 106 to three-way stop cock or first three-way joint 110; eighth tubing 129 transfers post adsorption ultrafiltrate from three-way stop cock or first three-way joint 110 to second three-way joint 125 joining fourth tubing 107 which transfers filtered blood along with the post adsorption ultrafiltrate to mammal 100, such as a human; and ninth tubing 121 transfers post adsorption ultrafiltrate from three-way stop cock or first three-way joint 110 to waste reservoir 119. Single ultrafiltrate pump 106 and associated tubing implement step 351 in FIG. 3; waste reservoir 119 and associated tubing implement step 310 in FIG. 3. Second three-way joint 125 and associated tubing implement step 312 in FIG. 3.

With respect to the tubing in FIG. 2, first tubing 201 transfers blood from mammal 200, such as a human, to blood pump 204; second tubing 203 transfers blood from blood pump 204 to hemofilter 202; third tubing 205 transfers the filtered blood filtered by hemofilter 202 to second three-way joint 225; fourth tubing 207 transfers the filtered blood along with the post adsorption ultrafiltrate to mammal 200, such as a human; fifth tubing 212 transfers the ultrafiltrate to three-way stop cock or first three-way joint 210; sixth tubing 215 transfers the ultrafiltrate from three-way stop cock or first three-way joint 210 to adsorptive device 208; seventh tubing 229 transfers the post adsorption ultrafiltrate or ultrafiltrate stream 215 to first ultrafiltrate pump 206a; eighth tubing 223 transfers post adsorption ultrafiltrate from first ultrafiltrate pump 206a to second three-way joint 225 joining fourth tubing 207 which transfers filtered blood along with the post adsorption ultrafiltrate to mammal 200, such as a human; ninth tubing 225 transfers ultrafiltrate from three-way stop cock or first three-way joint 210 to second ultrafiltrate pump 206b; and tenth tubing 233 transfers ultrafiltrate from second ultrafiltrate pump 206b to waste reservoir 219. First ultrafiltrate pump 206a and associated tubing implement steps 411 and 412 in FIG. 4; second ultrafiltrate pump 206b and waste reservoir 219 and associated tubing implement steps 409 and 410 in FIG. 4.

Figure 6:
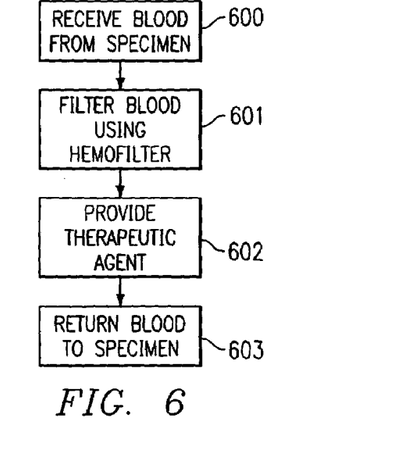
FIG. 6 illustrates a method for providing therapeutic agents with hemofiltration according to one embodiment of the present invention.

FIG. 6 illustrates a method for providing therapeutic agents with hemofiltration according to selected embodiments of the present invention. The method may be used with one of the systems disclosed in FIGS. 1A, 1B, 2, and 7, or other systems configurable to provide therapeutic agents and hemofiltration.

The method begins at step 600 where a system receives blood from a mammal, such as a human. In one embodiment, blood is continuously withdrawn from a mammal, preferably from a major blood vessel cannulated thereby allowing continuous withdrawal of blood from a mammal. A pump may also be provided for continuous withdrawal and transfer of blood from a mammal. The method then proceeds to step 601 where a hemofilter filters the blood.

In a specific embodiment, the hemofilter used to filter blood may include a large pore hemofiltration membrane configured to provide molecular weight exclusion limits of 100,000 to 150,000 Daltons. In this manner, a wide range of different immune mediators may be removed from the blood.

Other embodiments may include incorporating an adsorptive device at step 601. Adsorptive devices, such as those disclosed above, may be provided for adsorbing additional inflammatory mediators. An adsorptive device may be configured with one or more chambers and may be included within a hemofilter or provided as an additional component within a hemofiltration system. The adsorption device's chambers may include selective adsorbent materials having adsorptive characteristics and capacities for adsorbing during the course of any Inflammatory Mediator Related Disease. Therefore, various adsorbent materials may be used in order to provide a range of chemical binding characteristics and capacities needed for removal of many inflammatory mediators from ultrafiltrate.

Upon filtering the blood, the method may proceed to step 601 where a therapeutic agent is provided to the filtered blood. The therapeutic agent may be provided or integrated into the blood in certain dose adjusted amounts thereby providing a therapeutic agent in association with hemofiltration of blood.

In one embodiment, a therapeutic agent may be a pharmaceutical agent developed to treat an Inflammatory Mediator Related Disease. Pharmaceutical agents may include, but are not limited to, venerable allopurinol, elastase inhibitors, and prostaglandin inhibitors. Other pharmaceutical agents may be used as they are developed and become available. The pharmaceutical agent may be provided in a predetermined dosage amount such that, upon providing the pharmaceutical agent an effective amount of therapy is provided to a specimen or mammal. In this manner, hemofiltration used in conjunction with a pharmaceutical agent may reduce undesirable effects or disorders in an inflammatory response of a mammal.

In another embodiment, the therapeutic agent may be directed towards alleviation of a coagulation disorder. For example, the therapeutic agent may be activated protein C, sometimes referred to as recombinant activated protein C. The therapeutic agent may also be full length protein C or other species and derivatives having full protein C proteolytic, amidolytic, esterolytic and biological (anticoagulant or profibrinolytic) activities. See U.S. Pat. No. 6,008,199 entitled "Methods For Treating Hypercoagulable States Or Acquired Protein C Deficiency" for examples of protein C variants useable in treating coagulation disorders. Human protein C and its derivatives and variants may be used in many embodiments of the invention. In some embodiments of the invention, protein C may be used for treatment of problems other than coagulation disorders, or to treat the effects of coagulation disorders.

In still another embodiment, the therapeutic agent may be a biological agent developed to treat Systemic Inflammatory Response Syndrome/Multiple Organ System Dysfunction Syndrome/Multiple Organ System Failure or Compensatory Anti-inflammatory Response Syndrome. Biological agents may include, but are not limited to, monoclonal antibodies or receptor antagonists such as anti-tumor necrosis factor, interleukin 1 receptor antagonist, and various endotoxin antibodies. Other biological agents may be used as they are developed and become available. The biological agent may be provided in a predetermined dosage amount such that, upon providing the biological agent, an effective amount of therapy is provided to a mammal. In this manner, hemofiltration used in conjunction with a biological agent may reduce undesirable effects or disorders in an inflammatory response of a mammal.

Upon providing a therapeutic agent to the blood, the method then proceeds to step 603 where the blood is returned to the mammal. Therefore, the method of FIG. 6 provides hemofiltration of blood received from a mammal, such as a human. The hemofiltration may be used in conjunction with a therapeutic agent, such as a pharmaceutical agent and/or a biological agent, thereby providing enhanced therapy of an Inflammatory Mediator Related Disease. In this manner, excessive and destructive inflammatory activity may be abated allowing the inflammatory system of the mammal to return to a more physiologic level.

Figure 7:
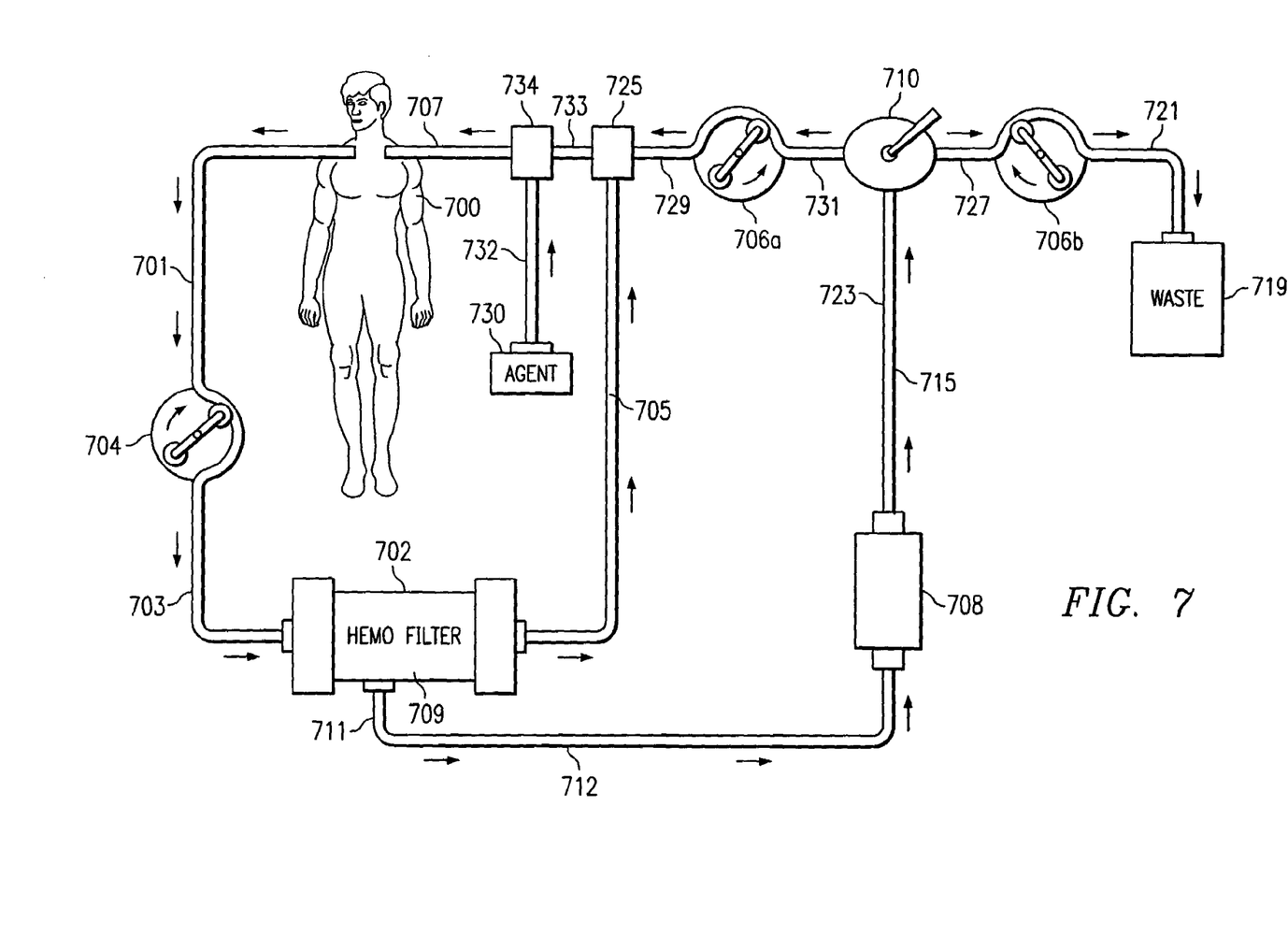
FIG. 7 illustrates a system for providing therapeutic agents and hemofiltration according to one embodiment of the present invention.

FIG. 7 illustrates a system for providing hemofiltration with therapeutic agents according to one embodiment of the present invention. The system illustrated in FIG. 7 is similar to the systems illustrated in FIGS. 1A, 1B, and 2 and may include like or similar components or features. FIG. 7 illustrates one configuration of providing a hemofiltration system incorporating therapeutic agents for an Inflammatory Mediator Related Disease.

During operation, blood may be continuously withdrawn from mammal 700, such as a human into tube 701 via a cannulated major blood vessel allowing continuous withdrawal of blood by blood pump 704. The amount of blood continuously pumped may depend on the condition of mammal 700, such as a human and may be determined on a case by case basis.

Blood is transferred from mammal 700, such as a human to hemofilter 702 via tube 701, blood pump 704 and tube 703. Tube 705 transfers the filtered blood to first three-way joint 725. Tube 712 coupled to hemofilter 702 transfers ultrafiltrate 711 to adsorptive device 708 where, via tube 723, adsorptive device transfers post adsorptive ultrafiltrate 715 to three-way stop cock 710. Three-way stopcock 710 allows transfer of post absorption ultrafiltrate 715 to first ultrafiltrate pump 706a via tube 731 and second ultrafiltrate pump 706b via tube 727. Second ultrafiltrate pump 706b and tube 721 transfer post adsorption ultrafiltrate from second ultrafiltrate pump 706b to waste reservoir 719.

First ultrafiltrate pump 706a pumps post adsorption ultrafiltrate 715 to first three-way joint 725 via tube 731 and tube 729. First three-way joint 725 transfers filtered blood and post adsorption filtrate 715 to second three-way joint 734. Therapeutic agent 730 is transferred to second three-way joint via tube 732 where tube 707 transfers therapeutic agent 730, post adsorption ultrafiltrate 715 and blood to mammal 700, such as a human. In this manner, the system illustrated in FIG. 7 provides hemofiltration of blood from a mammal in conjunction with a therapeutic agent, thereby providing enhanced therapy of an Inflammatory Mediator Related Disease.

In a specific embodiment, hemofilter 702 may include a large pore hemofiltration membrane configured to provide molecular weight exclusion limits of 100,000 to 150,000 Daltons. In this manner, a wide range of different immune mediators may be removed from the blood.

Additionally, in a specific embodiment therapeutic agent 730 may provide variable dose adjusted pharmaceutical agents and/or biological agents as needed by mammal 700, such as a human. In one embodiment, a therapeutic agent may be a pharmaceutical agent developed to treat an Inflammatory Mediator Related Disease. Pharmaceutical agents may include, but are not limited to, venerable allopurinol, elastase inhibitors, prostaglandin inhibitors, and protein C. Other pharmaceutical agents may be used as they are developed and become available. The pharmaceutical agent may be provided in a predetermined dosage amount such that, upon providing the pharmaceutical agent an effective amount of therapy is provided to a mammal.

In another embodiment, the therapeutic agent may be a biological agent developed to treat an Inflammatory Mediator Related Disease. Biological agents may include, but are not limited to, monoclonal antibodies or receptor antagonists such as anti-tumor necrosis factor, interleukin 1 receptor antagonist, and various endotoxin antibodies. Other biological agents may be used as they are developed and become available. The biological agent may be provided in a predetermined dosage amount such that, upon providing the biological agent, an effective amount of therapy is provided to a mammal. Therefore, as different types or new therapeutic agents become available, the system illustrated in FIG. 7 may be configured to provide the newly available therapeutic agents with hemofiltration thereby providing an enhanced therapy of an Inflammatory Mediator Related Disease.

In one embodiment, a therapeutic agent may be provided to mammal 700, such as a human, without the use of therapeutic agent 730, tube 732, second three-way joint 734, and tube 707. For example, a predetermined dosage amount of a therapeutic agent may be intravenously provided to mammal 700, such as a human, using an separate therapeutic agent system (not shown) configured to provide therapeutic agents in association with hemofiltered blood. In this embodiment, mammal 700, such as a human, may receive hemofiltered blood via tube 707 and variable dose adjusted therapeutic agents via a separate tube (not shown). In this manner, a hemofiltration system may be provided in addition to a therapeutic agent system for providing enhanced therapy of an Inflammatory Mediator Related Disease.

Various modifications of the systems and methods described above are also included within the scope of the present invention. For instance, structural modifications may include the integration of hemofilter 102 in FIGS. 1A and 1B and hemofilter 202 in FIG. 2 with adsorptive device 108 (in FIGS. 1A and 1B) and adsorptive device 208 (in FIG. 2), both of which have one or more chambers containing adsorbent material of one or more types, with elimination of the additional tubing. In this embodiment ultrafiltrate formed in jacket of hemofilter 102 (in FIGS. 1A and 1B) and hemofilter 202 (in FIG. 2) may be presented directly to adsorbent material contained with in hemofilter jacket or in a chamber or chambers directly contiguous with hemofilter jacket. The chamber containing ultrafiltrate may be drained by ultrafiltrate line. Ultrafiltrate may be continuously pumped and apportioned for discard or returned to mammal 100 (in FIGS. 1A and 1B) and mammal 200 (in FIG. 2), such as a human. In addition, the configuration of ultrafiltrate lines may be modified to provide for infusion of ultrafiltrate into mammal 100 (in FIGS. 1A and 1B) or mammal 200 (in FIG. 2), such as a human, via a vascular cannula in a blood vessel and separate from the hemofiltration circuit. Furthermore, the ultrafiltrate return pump and the ultrafiltrate discard pump in the embodiments shown and discussed above may be combined into a single two head ultrafiltrate pump system. While the ultrafiltrate return pump and the ultrafiltrate discard pump are shown in the figures as two separate pumps, it is within the scope of the invention to combine two pumps into a single pump, and thus, the separate pumps may be interpreted as two parts of a single pump.

Hemofiltration, particularly with a 100 to 150 kD filter, removes many excess circulating inflammatory mediators which respectively characterize Systemic Inflammatory Response Syndrome/Multiple Organ System Dysfunction Syndrome/Multiple Organ System Failure, or Compensatory Anti-inflammatory Response Syndrome. During either condition, it may be desirable to actually supplement inflammatory mediators or provide some other therapeutic agent to augment the system in abatement. In particular, during Systemic Inflammatory Response Syndrome/Multiple Organ System Dysfunction Syndrome/Multiple Organ System Failure when pro-inflammatory inflammatory mediators are in excess, in addition to performance of hemofiltration to remove excess pro-inflammatory inflammatory mediators, the administration of anti-inflammatory inflammatory mediators or therapeutic agents may be useful to additionally abate or otherwise modulate the pro-inflammatory systemic inflammatory response. Similarly, during Compensatory Anti-inflammatory Response Syndrome hemofiltration may remove many excess anti-inflammatory inflammatory mediators which may ameliorate immune suppression, in addition, administration of pro-inflammatory inflammatory mediators or other therapeutic agents to promote immune responsiveness, may ameliorate immune suppression of Compensatory Anti-inflammatory Response Syndrome.

Modifications of the adsorptive device may be determined by the Inflammatory Mediator Related Disease to be treated and the phase of the disease. Various regions of the inflammatory mediator network are dominant at different phases of an Inflammatory Mediator Related Disease and different Inflammatory Mediator Related Diseases exhibit different patterns of inflammatory mediator networking. Thus a different adsorbent material or materials, or different groupings of adsorbent materials may be needed for different Inflammatory Mediator Related Diseases in their different phases. Thus different adsorptive devices may be developed as more is learned of Inflammatory Mediator Related Diseases and their phases. Adsorptive devices may contain a fixed adsorbent material or a fixed combination of adsorbent materials. Alternatively, an adsorptive device may be configured with different, interchangeable modules of adsorbent materials to be adapted to the changing dominance of the inflammatory mediator network. The modules may consist of one or more chambers containing adsorbent material of one or more types. The adsorptive device may be designed to accept modules of adsorptive materials inserted in place as dictated by mammal need and operator assessment.

Different configurations of adsorbent materials may be used. Adsorbent materials exhibit chemical characteristics which determine what physical form will provide the greatest stability in flowing ultrafiltrate. Adsorbent material may remain irreversibly bound to its supporting matrix, or in the case of beads (e.g. polysulfone, polyacrylonitrile, etc) or particulates (e.g. charcoal) inescapably contained in mesh or other containment device. Adsorbent material, matrix, and containment material are preferably not allowed to dissolve, dissociate or fragment into the ultrafiltrate to be infused into the mammal. Adsorbent material, matrix, and containment material may be configured to provide physical durability, and adequate porosity and configuration for optimal presentation of adsorbent material to flowing ultrafiltrate. Some configurations of matrix are shown in FIGS. 5A, 5B, and 5C. Adsorptive devices of one or more chambers containing adsorbent material of one or more types may be used in series, in which ultrafiltrate flows from the first to subsequent adsorptive devices. The sequence, number and type of adsorptive devices may be determined by operator to meet the needs of the mammal. Alternatively, the ultrafiltrate stream may be divided by a manifold with distribution of ultrafiltrate to adsorptive devices arranged in a parallel configuration, with each line from each adsorptive device either returned to a manifold and reunited into a single ultrafiltrate line, or each line individually apportioned for return to mammal and discard.

Various components described specifically for the systems and methods described above may be used with other systems and methods, including those described specifically herein and other systems and methods not specifically described. Appropriate uses will be apparent to one skilled in the art.

Although the present invention has been described in detail, it should be understood that the various changes, substitutions, and alterations could be made hereto without departing from the spirit and scope of the invention as defined by the appended claims.

The invention claimed is:

1. A method for treating a disease in a mammal comprising:
   pumping blood from the mammal using a blood pump;
   transferring the blood from the blood pump to a hemofilter;
   removing an ultrafiltrate from the blood using the hemofilter to create a filtered blood stream and an ultrafiltrate stream;
   transferring the ultrafiltrate stream from the hemofilter to an adsorptive device containing at least one fixed adsorbent material;
   selectively removing an inflammatory mediator which causes Compensatory Anti-inflammatory Response Syndrome from the ultrafiltrate stream using the adsorbent material to create a post adsorption ultrafiltrate stream;
   combining at least a portion of the post adsorption ultrafiltrate stream with the filtered blood stream and returning the combined post adsorption ultrafiltrate stream and the filtered blood stream to the mammal;
   transferring a portion of the post adsorption ultrafiltrate stream which is not returned to the mammal to a waste reservoir; and
   providing at least one therapeutic agent to the blood.

2. The method of claim 1 further comprising transferring the post adsorption ultrafiltrate stream from the adsorptive device using an ultrafiltrate pump.

3. The method of claim 1 further comprising:
   transferring the post adsorption ultrafiltrate stream from the adsorptive device using a first ultrafiltrate pump; and
   transferring any portion of the post adsorption ultrafiltrate stream which is not returned to the mammal to the waste reservoir using a second ultrafiltrate pump.

4. The method of claim 1 wherein the mammal has a disease selected from a group consisting of: Lupus erythematosis, Hemolytic Uremic Syndrome, Bullous Pemphigoid, pemphigus vulgaris, sepsis, fibromyalgia, rheumatoid conditions, chronic neuromuscular diseases, multiple sclerosis, Guillain-Barre syndrome, cryobulinemic vasculitis, chronic inflammatory demyelinating polyneuropathy, macular degeneration, chronic neuromuscular and multifocal motor neuropathy, coagulation disorders, and any combination thereof.

5. A method for treating Compensatory Anti-inflammatory Response Syndrome in a mammal comprising:
   performing hemofiltration on blood from the mammal using a hemofilter to generate an ultrafiltrate;
   transferring the ultrafiltrate to an adsorptive device containing at least one fixed adsorbent material;
   selectively removing an inflammatory mediator which causes Compensatory Anti-inflammatory Response Syndrome from the ultrafiltrate using the adsorbent material to create a post adsorption ultrafiltrate;
   returning at least a portion of the post adsorption ultrafiltrate to the mammal; and
   providing at least one therapeutic agent to the blood.

6. The method of claim 5, wherein the mammal has a disease selected from a group consisting of: Lupus erythematosis, Hemolytic Uremic Syndrome, Bullous Pemphigoid, pemphigus vulgaris, sepsis, fibromyalgia, rheumatoid conditions, chronic neuromuscular diseases, multiple sclerosis, Guillain-Barre syndrome, cryobulinemic vasculitis, chronic inflammatory demyelinating polyneuropathy, macular degeneration, chronic neuromuscular and multifocal motor neuropathy, coagulation disorders, and any combination thereof.

7. The method of claim 5, wherein the therapeutic agent comprises a biological agent.

8. The method of claim 5, wherein the therapeutic agent comprises a pharmaceutical agent.

9. The method of claim 5, wherein the therapeutic agent further comprises protein C or a protein C derivative.

10. The method of claim 9, further comprising the protein C or protein C derivative selected from a group consisting of: recombinant activated protein C, human protein C, proteolytic, amidolytic and esterolytic protein C, and any combination thereof.

11. The method of claim 9, further comprising the therapeutic agent selected from a group consisting of: monoclonal antibodies, receptor antagonists, anti-tumor necrosis factor, interleukin 1 receptor antagonists, endotoxin antibodies, allopurinol, elastase inhibitors, prostaglandin inhibitors, and any combination thereof.

12. A method for treating Compensatory Anti-inflammatory Response Syndrome in a mammal comprising:
   receiving blood from the mammal;
   filtering the blood using a hemofilter to remove an inflammatory mediator from the blood; and
   providing at least one biological therapeutic agent to the blood to reduce adverse inflammatory mediator effects associated with treating Compensatory Anti-inflammatory Response Syndrome.

13. A method for treating a disease in a mammal comprising:
   pumping blood from the mammal using a blood pump;
   transferring the blood from the blood pump to a hemofilter;
   removing an ultrafiltrate from the blood using the hemofilter to create a filtered blood stream and an ultrafiltrate stream;
   transferring the ultrafiltrate stream from the hemofilter to an adsorptive device containing at least one fixed adsorbent material;

selectively removing an inflammatory mediator which causes an Inflammatory Mediator Related Disease from the ultrafiltrate stream using the adsorbent material to create a post adsorption ultrafiltrate stream;

combining at least a portion of the post adsorption ultrafiltrate stream with the filtered blood stream and returning the combined post adsorption ultrafiltrate stream and the filtered blood stream to the mammal;

transferring a portion of the post adsorption ultrafiltrate stream which is not returned to the mammal to a waste reservoir; and providing at least one therapeutic agent to the blood.

14. The method of claim 13 further comprising transferring the post adsorption ultrafiltrate stream from the adsorptive device using an ultrafiltrate pump.

15. The method of claim 13 further comprising:

transferring the post adsorption ultrafiltrate stream from the adsorptive device using a first ultrafiltrate pump; and transferring any portion of the post adsorption ultrafiltrate stream which is not returned to the mammal to the waste reservoir using a second ultrafiltrate pump.

16. The method of claim 13, wherein the mammal has a disease selected from a group consisting of: Lupus erythematosis, Hemolytic Uremic Syndrome, Bullous Pemphigoid, pemphigus vulgaris, sepsis, fibromyalgia, rheumatoid conditions, chronic neuromuscular diseases, multiple sclerosis, Guillain-Barre syndrome, cryobulinemic vasculitis, chronic inflammatory demyelinating polyneuropathy, macular degeneration, chronic neuromuscular and multifocal motor neuropathy, coagulation disorders, and any combination thereof.

17. The method of claim 13, wherein the therapeutic agent comprises a biological agent.

18. The method of claim 13, wherein the therapeutic agent comprises a pharmaceutical agent.

19. The method of claim 13, wherein the therapeutic agent further comprises protein C or a protein C derivative.

20. The method of claim 19, further comprising the protein C or protein C derivative selected from a group consisting of: recombinant activated protein C, human protein C, proteolytic, amidolytic and esterolytic protein C, and any combination thereof.

21. The method of claim 13, further comprising the therapeutic agent selected from a group consisting of: monoclonal antibodies, receptor antagonists, anti-tumor necrosis factor, interleukin 1 receptor antagonists, endotoxin antibodies, allopurinol, elastase inhibitors, prostaglandin inhibitors, and any combination thereof.

* * * * *